United States Patent [19]

Castaldi et al.

[11] Patent Number: 5,055,576
[45] Date of Patent: Oct. 8, 1991

[54] PHOTOCHROMATIC AND THERMOCHROMATIC SPIRO-OXAZEPIN-OXAZINE COMPOUNDS AND THE PROCESS FOR THEIR PREPARATION

[75] Inventors: Graziano Castaldi, Briona; Pietro Allegrini, San Donato Milanese, both of Italy

[73] Assignee: Enichem Synthesis, S.p.A., Palermo, Italy

[21] Appl. No.: 622,710

[22] Filed: Dec. 6, 1990

[30] Foreign Application Priority Data

Dec. 12, 1989 [IT] Italy .................. 22659 A/89

[51] Int. Cl.$^5$ .................. G02F 1/00; G02B 5/23; F21V 9/04; C07D 223/14
[52] U.S. Cl. .................. 540/543; 252/583; 252/586; 252/589
[58] Field of Search ............... 252/582, 583, 586, 589; 540/543

[56] References Cited

U.S. PATENT DOCUMENTS

| | | |
|---|---|---|
| 3,231,584 | 1/1966 | Berman et al. |
| 3,391,149 | 7/1968 | Easton et al. .................. 540/543 |
| 3,562,172 | 2/1971 | Hisatake Ono et al. .................. 252/586 |
| 3,578,602 | 5/1971 | Hisatake Ono et al. .................. 252/586 |
| 3,876,659 | 4/1975 | Houlihan et al. .................. 540/543 |
| 4,215,010 | 7/1980 | Hovey et al. .................. 252/586 |
| 4,342,668 | 8/1982 | Hovey et al. .................. 252/586 |

FOREIGN PATENT DOCUMENTS 0134633 3/1985 European Pat. Off. .
0141407 5/1985 European Pat. Off. .

Primary Examiner—John S. Maples
Assistant Examiner—Philip Tucker
Attorney, Agent, or Firm—Hedman, Gibson, Costigan & Hoare

[57] ABSTRACT

New photochromatic and thermochromatic compounds of the spiro-oxazepin-oxazine class are definable by the general formula (I):

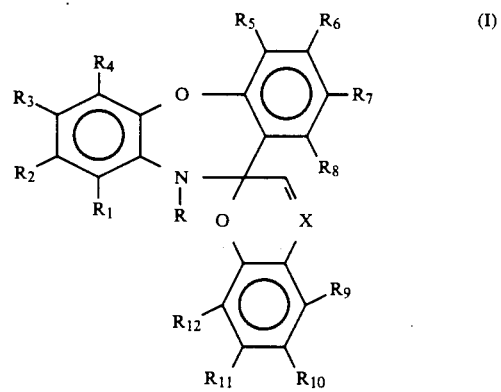

where the substituents R and $R_1$–$R_{12}$ are as defined in the description.

The process for the preparation of the compounds (I) is described, as is their use as photochromatic and thermochromatic agents.

3 Claims, No Drawings

PHOTOCHROMATIC AND THERMOCHROMATIC SPIRO-OXAZEPIN-OXAZINE COMPOUNDS AND THE PROCESS FOR THEIR PREPARATION

This invention relates to new photochromatic and thermochromatic spiro-oxazepin-oxazine compounds, their preparation and their use. Photochromatic compounds are substances having the characteristic of reversibly changing their colour and/or degree of light transmission when exposed to certain types of electromagnetic radiation and sunlight, to return to their initial colour and light transmission state when the light source is removed.

Thermochromatic compounds are substances having the characteristic of reversibly changing colour and/or degree of light transmission when exposed to a heat source, to return to their initial colour and light transmission state when the heat source is removed.

There are many known substances possessing photochromatic and/or thermochromatic characteristics and pertain to various classes of organic and inorganic compounds, as described for example in "Photochromism", G. H. Brown (Ed.), vol. III, of the Weissberger series "Techniques of Organic Chemistry", Wiley Interscience, New York (1971).

The most well known photochromatic and/or thermochromatic organic compounds pertain to the spiro-indoline-oxazine and spiro-indoline-pyran classes. These compounds are able to confer photochromatic and/or thermochromatic characteristics on polymerized organic materials used in solar filters, optical articles, optical memories, printing, photography, fabrics, decorative articles and toys.

For this known art reference should be made to the description of U.S. Pat. Nos. 3,562,172, 3,578,602, 4,215,010 and 4,342,668, and to European patent applications publication Nos. 134,633 and 141,407. These compounds of the known art have however the drawback of limited fatigue strength when subjected to repeated photochemical and/or thermal coloration and decoloration cycles. Their resistance to ageing by exposure to sunlight is also generally unsatisfactory, particularly at higher than ambient temperature. The object of the present invention is to overcome the aforesaid drawbacks of the known art by providing a new class of photochromatic and/or thermochromatic spiro-oxazepin-oxazine compounds having high fatigue strength and high ageing resistance even at temperatures well above ambient temperature.

In accordance therewith a first aspect of the present invention is the provision of new photochromatic and thermochromatic compounds of the spiro-oxazepin-oxazine class definable by the general formula (I):

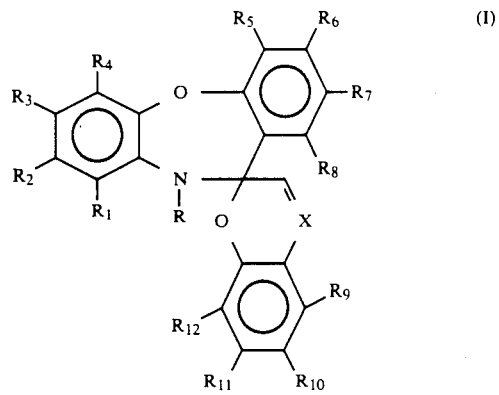

where:

X represents a nitrogen atom or a CH group;

R represents a hydrogen atom; a linear or branched $C_1$–$C_5$ alkyl group; a said $C_1$–$C_5$ alkyl group substituted with 1 to 5 atoms of halogen chosen from fluorine, chlorine, bromine and iodine; a $C_1$–$C_5$ alkoxy group; a $C_1$–$C_5$ carboxyalkyl group; a cyano group; a $C_2$–$C_5$ alkenyl group; a phenyl group; or a benzyl group;

$R_1$ to $R_{12}$, which can be identical or different, each independently represent a hydrogen atom; a linear or branched $C_1$–$C_5$ alkyl group; a $C_2$–$C_5$ alkenyl group; a benzyl group; a halogen atom chosen from fluorine, chlorine, bromine and iodine; a hydroxy group; a $C_1$–$C_5$ alkoxy group; an amino group; a $C_1$–$C_5$ monoalkyl amino group; a $C_1$–$C_5$ dialkyl amino group; a $C_3$–$C_7$ cycloalkyl amino group; a carboxyl group; a $C_1$–$C_5$ carboxyalkyl group; a carboxyamide group; a $C_1$–$C_5$ N-alkyl substituted or $C_1$–$C_5$ N,N-dialkyl substituted carboxyamide group; a cyano or nitro group; or any adjacent two taken from $R_9$, $R_{10}$, $R_{11}$ and $R_{12}$ jointly represent a condensed benzene nucleus without substituents or carrying from 1 to 3 substituents chosen from those described for $R_1$–$R_{12}$.

In the preferred embodiment, in formula (I) R is a hydrogen atom or methyl radical; $R_1$ to $R_8$ each independently represent a hydrogen atom or methyl radical; $R_9$ to $R_{12}$ each independently represent a hydrogen atom, methoxy radical or nitro radical; or two adjacent thereof represent jointly a condensed benzene nucleus without substituents or carrying from 1 to 3 substituents chosen from methoxy, nitro and carboxymethyl groups.

Specific examples of preferred photochromatic compounds according to the present invention are:

10-methyl spiro dibenzo[b,f]-1,4-oxazepin-11,3'-[11H]naphtho-(2,1-b)-(1,4-oxazine);

10-methyl-8'-methoxy-6'-nitro spiro dibenzo[b,f]-1,4-oxazepin-11,2'-[11H]benzo-(2,1-b)-[3H]pyran;

10-methyl-8'-methoxy spiro dibenzo[b,f]-1,4-oxazepin-11,3'-[11H]naphtho-(2,1-b)-(1,4-oxazine); and methyl ester of 10-methyl spiro dibenzo[b,f]-1,4-oxazepin-11,3'-[11H]naphtho-(2,1-b)-1,4-oxazine-8'-carboxylic acid.

The compounds of the present invention in which X=N in formula (I) can be prepared by reacting a nitroso derivative definable by the formula (II A) or a tautomer thereof definable by the formula (II B):

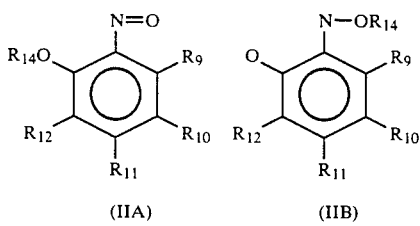

with a compound of general formula (III):

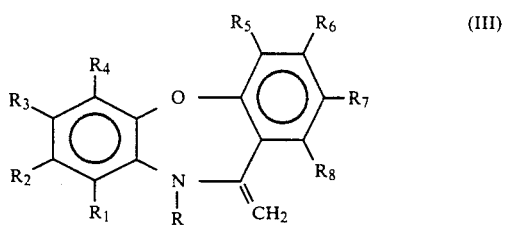

where the substituents R and $R_1$–$R_{12}$ are as heretofore defined and $R_{14}$ represents a hydrogen atom, a $C_1$–$C_5$ carbonylalkyl group, a $C_1$–$C_5$ sulphonyloxyalkyl group or a sulpharyl group.

Generally, the reaction is conducted by adding the compound (III) to a solution of the compound (IIA) or (IIB) in an inert organic solvent, possibly in the presence of a tertiary amine, operating at a temperature of between 0° and 150° C. and preferably between 0° and 80° C. for a time of between about 1 minute and 24 hours. The compounds (IIA) and (IIB) can be prepared by a known method, such as that described in Organic Synthesis Collective Volume 3, page 411, or in U.S. Pat. No. 3,285,972.

The compounds (III) can be prepared by known methods from 11-methyl-dibenzo[b,f]-1,4-oxazepin, as described for example in J. Chem. Soc. (1962) 2367; J. Chem. Soc. (1953) 1079; and J. Chem. Soc. Perkin I (1976) 1279.

The compounds of the present invention in which X=CH in formula (I) can be prepared by reacting a compound (III) with a salicylaldehyde of formula (IV):

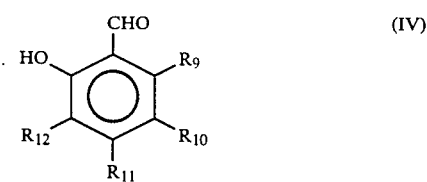

where the substituents $R_9$–$R_{12}$ are as heretofore described. The reaction is generally conducted by adding the compound (III) to a solution of the compound (IV) in an inert organic solvent, operating at a temperature of between 0° and 150° C. and preferably between 0° and 80° C. for a time of between about 1 minute and 24 hours.

Inert solvents suitable for the aforesaid reactions can be chosen from aliphatic or aromatic hydrocarbons (such as pentane, hexane, heptane, benzene, toluene and xylene); chlorinated aliphatic or aromatic hydrocarbons (such as dichloromethane, 1,2-dichloroethane and chlorobenzene); aliphatic or aromatic ethers (such as diethyl ether, tetrahydrofuran and diphenylether); alcohols (such as methanol, ethanol, isopropanol and n-butanol); esters (such as ethyl acetate); amides (such as dimethylformamide); nitriles (such as acetonitrile); carbonates (such as dimethylcarbonate); and water.

The compounds (IIA), (IIB) and (IV) can be used in the reaction in quantities varying from 0.1 to 10 moles per mole of the compound (III), but equimolecular quantities are preferably used.

If the reaction is conducted in the presence of a tertiary amine this can be used in a quantity of between 0.1 and 2 moles per mole of the compound (IIA) or (IIB), but equimolecular quantities are preferably used. Examples of tertiary amines suitable for the purpose are: triethylamine, pyridine, N-methylpyridine, N,N-dimethyl-4-aminopyridine and N-methyl-morpholine.

On termination of the reaction the compounds (I) are isolated by normal methods, for example by evaporating the solvent under vacuum, and then purified for example by crystallization or chromatography. Solvents suitable for crystallization include pentane, hexane, heptane, toluene, ethyl ether, methanol, ethanol, isopropanol, n-butanol, tetrahydrofuran, acetone, methylethylketone, ethyl acetate, dimethylcarbonate, acetonitrile and relative mixtures.

The photochromatic and thermochromatic spirooxazepin-oxazine compounds according to the present invention can be used to confer photochromatic and thermochromatic characteristics on articles of polymerized organic materials used as solar filters, optical articles, optical memories, prints, paper, photographs, fabrics, decorative articles and toys. In particular these compounds are useful in applications requiring high fatigue strength when subjected to repeated cycles of photochemical and/or thermal coloration and decoloration and a high resistance to ageing by exposure to sunlight, particularly at higher than ambient temperatures up to about 150° C.

The following experimental examples are given to better illustrate the present invention.

EXAMPLE 1

Preparation of 10-methyl-11-methylene[11H]dibenzo[b,f]-1,4-oxazepin

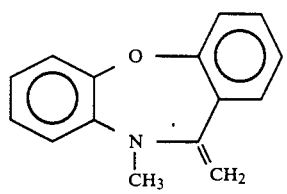

Dimethylsulphate (5.67 g; 45 mmoles) is added at ambient temperature (20°–25° C.) under stirring to a solution of 11-methyldibenzo[b,f]-1,4-oxazepin (9 g; 40 mmoles) in toluene (90 ml). The resultant solution is heated to 90° C. for 2 hours, cooled to ambient temperature and then 250 ml of 20 wt % aqueous sodium hydroxide are added, the aqueous and organic phases then being separated.

The toluene phase is washed with water, dried with sodium sulphate and the solvent evaporated under vacuum. The residue obtained is subjected to silica gel chromatography (eluent ethyl ether: n-hexane 1:3 by volume) to give the required product of the title.

¹H-NMR (200 MHz, CDCl₃-TMS) δ (ppm): 2.67 (3H, s, CH₃-N), 6.5-7.8 (10H, m, aromatic and olefinic protons).

Elemental analysis: Calculated: C 80.7%; H 5.8%; N 6.3%. Found: C 81.5%; H 5.5%; N 6.2%.

EXAMPLE 2

Preparation of 10-methyl spiro dibenzo[b,f]-1,4-oxazepin-11,3'-[11H]naphtho-(2,1-b)-(1,4-oxazine)

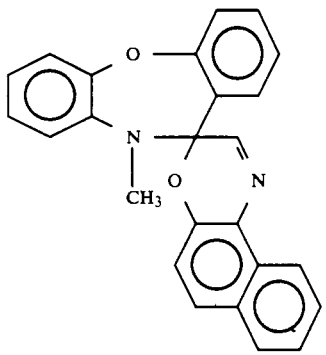

10-methyl-11-methylene-[11H]dibenzo[b,f]-1,4-oxazepin (3 g; 13.5 mmoles) (prepared as described in Example 1) is added to a suspension of 1-nitroso-2-naphthol (2.3 g; 13.5 mmoles) in toluene (50 ml). The mixture is heated to 90° C. for 12 hours and then cooled to ambient temperature, the solvent finally being evaporated under vacuum. The residue is crystallized from acetone to give the required compound of the title.

¹H-NMR (200 MHz, CDCl₃-TMS) δ (ppm): 2.92 (3H, s, CH₃-N), 6.9-8.1 (15H, m).

Mass (m/e): 378.

Elemental analysis: Calculated: C 79.4%; H 4.8%; N 7.4%. Found: C 79.8%; H 4.5%; N 7.2%.

EXAMPLE 3

Preparation of 10-methyl-8'-methoxy-6'-nitro spiro dibenzo[b,f]-1,4-oxazepin-11,2'-[11H]benzo-(2,1-b)-[3H]pyran

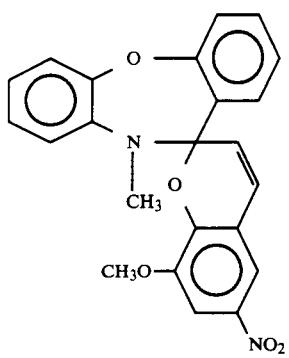

10-methyl-11-methylene-[11H]dibenzo[b,f]-1,4-oxazepin (2.23 g; 10 mmoles) is added to a suspension of 2-hydroxy-3-methoxy-5-nitrobenzaldehyde (1.77 g: 0.9 mmoles) in ethanol (40 ml). The mixture is heated to reflux temperature for 3 hours, then cooled to ambient temperature. The residue formed is filtered off, washed with ethanol and dried under vacuum to give the required compound of the title.

¹H-NMR (200 MHz, CDCl₃-TMS) δ (ppm): 2.78 (3H, s, CH₃-N), 4.04 (s, 3H, OCH₃), 6.5-7.8 (12H, m).

Elemental analysis: Calculated: C 71.5%; H 4.7%; N 7.2%. Found: C 72.0%; H 4.5%; N 7.2%.

EXAMPLE 4

Preparation of 10-methyl-8'-methoxy spiro dibenzo[b,f]-1,4-oxazepin-11,3'-[11H]naphtho-(2,1-b)-(1,4-oxazine)

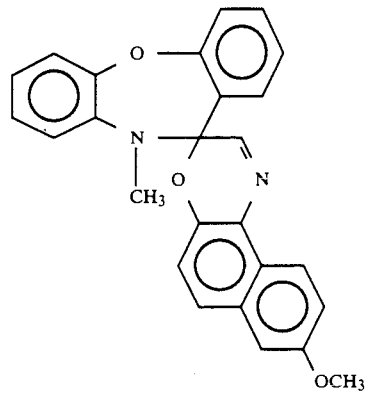

10-methyl-11-methylene-[11H]dibenzo[b,f]-1,4-oxazepin (2.22 g; 10 mmoles) is added to a suspension of 1-nitroso-6-methoxy-2-naphthol (2.03 g: 10 mmoles) in toluene (30 ml). The mixture is heated to 90° C. for 12 hours, then cooled to ambient temperature, the solvent being finally evaporated under vacuum. The residue obtained is subjected to silica gel chromatography (eluent n-hexane:ethyl ether 7:3 by volume) to give the required product of the title.

¹H-NMR (200 MHz, CDCl₃-TMS) δ (ppm): 2.90 (3H, s, CH₃-N), 3.93 (s, 3H, OCH₃), 6.8-8.2 (14H, m).

Mass (m/e): 408.

Elemental analysis: Calculated: C 76.5%; H 4.9%; N 6.9%. Found: C 75.8%; H 4.8%; N 6.7%.

EXAMPLE 5

Preparation of the methyl ester of 10-methyl spiro dibenzo[b,f]-1,4-oxazepin-11,3'-[11H]naphtho-(2,1-b)-1,4-oxazine-8-carboxylic acid

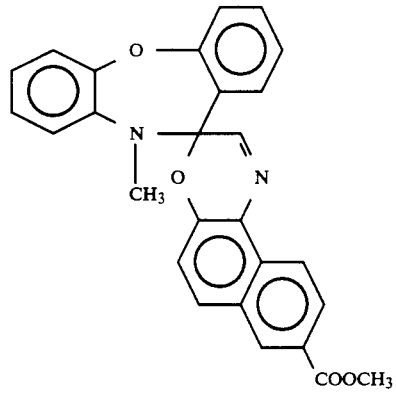

10-methyl-11-methylene-[11H]dibenzo[b,f]-1,4-oxazepin (2.22 g; 10 mmoles) is added to a suspension of 2-hydroxy-1-nitroso-6methoxy-2-naphthol methyl ester (2.31 g: 10 mmoles) in toluene (30 ml). The mixture is heated to 90° C. for 12 hours, then cooled to ambient temperature, the solvent being finally evaporated under vacuum. The residue obtained is subjected to silica gel chromatography (eluent n-hexane:ethyl ether 1:1 by volume) to give the required product of the title.

$^1$H-NMR (200 MHz, CDCl$_3$-TMS) δ (ppm): 2.93 (3H, s, CH$_3$-N), 3.53 (s, 3H, OCH$_3$), 6.8–8.3 (14H, m).

Mass (m/e): 437.

Elemental analysis: Calculated: C 74.1%; H 4.8%; N 6.4%. Found: C 73.7%; H 4.7%; N 6.4%.

Physico-Chemical Determination of Photochromism and Thermochromism

The spiro-oxazepin-oxazines generally demonstrate photochromatic behaviour, ie their UV-visible absorption spectrum in solution, in polymer matrix or of the product adsorbed on silica gel changes substantially on exposure to sunlight or to an artificial light source. These products are generally colourless in the solid state, whereas in their activated form the colour varies from red to blue. This effect is reversible, and in the dark, or on cooling, their initial colourless state returns.

For example, after evaporating the solvent, silica gel impregnated with solutions of 10-methyl spiro-dibenzo[b,f]-1,4-oxazepin-11,3'-[11H]naphtho-(2,1-b)-(1,4-oxazine) in toluene rapidly assumes an intense blue colour when exposed to sunlight and returns to its initial appearance when placed in the dark.

The spiro-oxazepin-oxazines generally demonstrate thermochromatic behaviour, ie their UV-visible absorption spectrum in solution or in polymer matrix changes substantially on heating to determined temperatures. This effect is reversible, ie they return to their initial state when below the activation temperature, as shown in the following table for 10 wt % solutions of the product 10-methyl spiro-dibenzo[b,f]-1,4-oxazepin-11,3'-[11H]naphtho-(2,1-b)-(1,4-oxazine) in the indicated solvents.

| Solvent | Activation temp. (°C.) | Colour | Deactivation temp. (°C.) |
| --- | --- | --- | --- |
| isopropanol | 60–65 | blue | 60 ± 2 |
| 1,2-dichloroethane | 70–75 | violet | 70 ± 2 |
| acetonitrile | 80–85 | violet | 80 ± 2 |
| toluene | 90–95 | pink | 90 ± 2 |

We claim:

1. A photochromatic and/or thermochromatic compound of the spirooxazepin-oxazine class definable by the general formula (I):

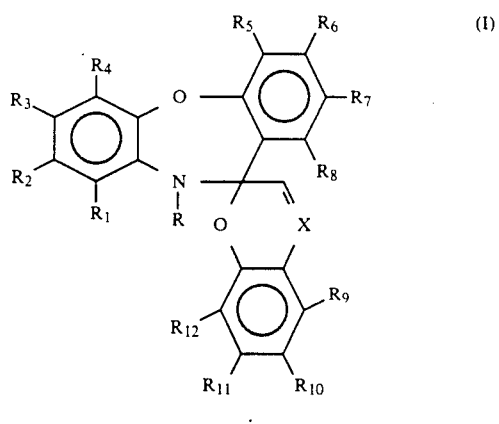

where:

X represents a nitrogen atom or a CH group;

R represents a hydrogen atom; a linear or branched C$_1$–C$_5$ alkyl group; a said C$_1$–C$_5$ alkyl group substituted with 1 to 5 atoms of halogen chosen from fluorine, chlorine, bromine and iodine; a C$_1$–C$_5$ alkoxy group; a C$_1$–C$_5$ carboxyalkyl group; a cyano group; a C$_2$–C$_5$ alkenyl group; a phenyl group; or a benzyl group;

R$_1$ to R$_{12}$, which can be identical or different, each independently represent a hydrogen atom; a linear or branched C$_1$–C$_5$ alkyl group; a C$_2$–C$_5$ alkenyl group; a benzyl group; a halogen atom chosen from fluorine, chlorine, bromine and iodine; a hydroxy group; a C$_1$–C$_5$ alkoxy group; an amino group; a C$_1$–C$_5$ monoalkyl amino group; a C$_1$–C$_5$ dialkyl amino group; a C$_3$–C$_7$ cycloalkyl amino group; a carboxyl group; a C$_1$–C$_5$ carboxyalkyl group; a carboxyamide group; a C$_1$–C$_5$ N-alkyl substituted or C$_1$–C$_5$ N,N-dialkyl substituted carboxyamide group; a cyano or nitro group; or any adjacent two taken from R$_9$, R$_{10}$, R$_{11}$ and R$_{12}$ jointly represent a condensed benzene nucleus without substituents or carrying from 1 to 3 substituents chosen from those described for R$_1$–R$_{12}$.

2. A photochromatic and/or thermochromatic compound as claimed in claim 1, characterised in that in formula (I) R is a hydrogen atom or methyl radical; R$_1$ to R$_8$ each independently represent a hydrogen atom or methyl radical; R$_9$ to R$_{12}$ each independently represent a hydrogen atom, methoxy radical or nitro radical; or two adjacent thereof represent jointly a condensed benzene nucleus without substituents or carrying from 1 to 3 substituents chosen from methoxy, nitro and carboxymethyl groups.

3. A photochromatic and/or thermochromatic compound as claimed in claim 1, selected from the group consisting of:

10-methyl spiro dibenzo[b,f]-1,4-oxazepin-11,3'-[11H]naphtho-(2,1-b)-(1,4-oxazine);

10-methyl-8'-methoxy-6'-nitro spiro dibenzo[b,f]-1,4-oxazepin-11,2'-[11H]benzo-(2,1-b)-[3H]pyran;

10-methyl-8'-methoxy spiro dibenzo[b,f]-1,4-oxazepin-11,3'-[11H]naphtho-(2,1-b)-(1,4-oxazine); and methyl ester of 10-methyl spiro dibenzo[b,f]-1,4-oxazepin-11,3'-[11H]maphtho-(2,1-b)-1,4-oxazine-8'-carboxylic acid.

* * * * *